(12) United States Patent
Schulte et al.

(10) Patent No.: US 7,052,595 B2
(45) Date of Patent: May 30, 2006

(54) GAS SENSOR FOR DETERMINING THE CONCENTRATION OF GAS COMPONENTS IN GAS MIXTURES AND USE THEREOF

(75) Inventors: Thomas Schulte, Stuttgart (DE); Thomas Wahl, Pforzheim (DE); Bernd Mueller, Leonberg (DE)

(73) Assignee: Robert Bosch GmbH, Stuttgart (DE)

( * ) Notice: Subject to any disclaimer, the term of this patent is extended or adjusted under 35 U.S.C. 154(b) by 419 days.

(21) Appl. No.: 10/149,940

(22) PCT Filed: Dec. 9, 2000

(86) PCT No.: PCT/DE00/04385

§ 371 (c)(1),
(2), (4) Date: Sep. 30, 2002

(87) PCT Pub. No.: WO01/44789

PCT Pub. Date: Jun. 21, 2001

(65) Prior Publication Data

US 2004/0104114 A1 Jun. 3, 2004

(30) Foreign Application Priority Data

Dec. 15, 1999 (DE) ................. 199 60 338

(51) Int. Cl.
*G01N 27/407* (2006.01)
(52) U.S. Cl. .................. 205/781; 205/784.5; 204/425; 73/23.31
(58) Field of Classification Search ........... 204/424, 204/425, 427; 205/781, 784.5; 73/23.31
See application file for complete search history.

(56) References Cited

U.S. PATENT DOCUMENTS

| 4,770,760 A | | 9/1988 | Noda et al. |
| 5,034,112 A | | 7/1991 | Murase et al. |
| 5,169,513 A | * | 12/1992 | Mase et al. ................. 204/429 |
| 6,019,881 A | * | 2/2000 | Kurosawa et al. .......... 204/424 |

FOREIGN PATENT DOCUMENTS

| DE | 196 52 968 | | 3/1998 |
| EP | 0 677 741 A2 | * | 10/1995 |
| EP | 0 678 740 | | 10/1995 |
| WO | WO 96/28722 | * | 9/1996 |

OTHER PUBLICATIONS

Inoue et a, J. Electrochem. Soc., 137(8), pp. 2523-2527, 1990.*
Logothetis et al, High-Temperature Oxygen Sensors Based on Electrochemical Oxygen Pumping, pp. 136-154, ACS Symposium Series 309, 19986.*

* cited by examiner

*Primary Examiner*—Kaj K. Olsen
(74) *Attorney, Agent, or Firm*—Kenyon & Kenyon LLP

(57) ABSTRACT

A gas sensor for determining the concentration of gas components in gas mixtures is used in particular to measure the concentration of nitrogen oxides in exhaust gases of internal combustion engines or in the interiors of motor vehicles. It contains an electrochemical measuring cell which includes a first electrode situated on a solid electrolyte and an additional electrode. The electrode is made of an oxide material containing lanthanum which at least catalytically decomposes nitrogen oxides. The pump current flowing between the electrodes is used as a measure of the nitrogen oxide concentration in the gas mixture.

8 Claims, 1 Drawing Sheet

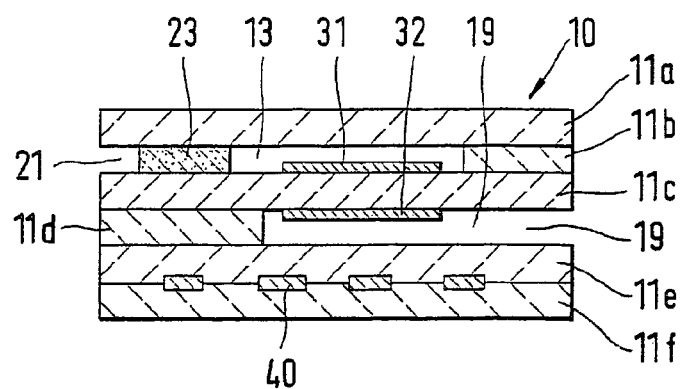
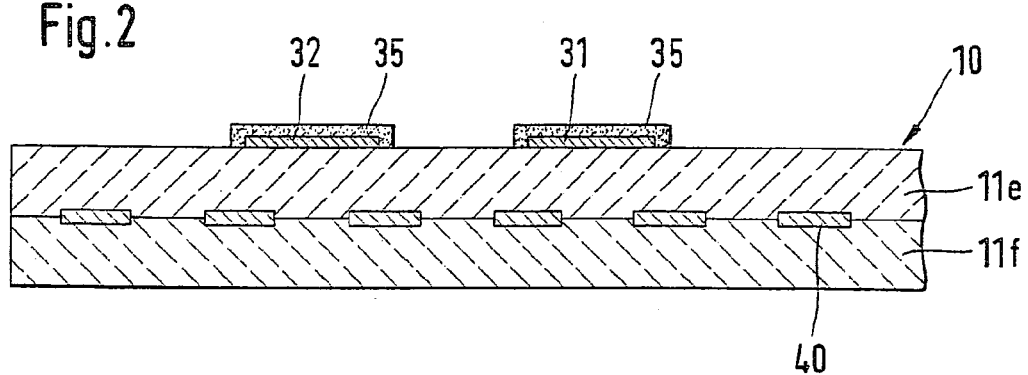
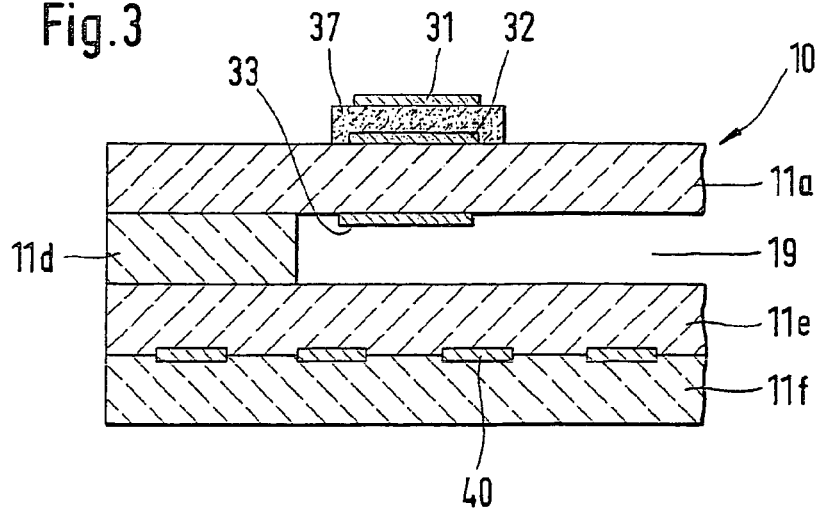

GAS SENSOR FOR DETERMINING THE CONCENTRATION OF GAS COMPONENTS IN GAS MIXTURES AND USE THEREOF

FIELD OF THE INVENTION

The invention relates to a gas sensor for determining gas components.

BACKGROUND INFORMATION

A sensor element for determining the $NO_x$ concentration in gas mixtures is known from German Published Patent Application No. 196 52 968 which is based on the interaction of two electrochemical pump cells. Two internal pump electrodes that are interconnected with a common external pump electrode arranged in a reference gas channel are located in a measuring gas space of the sensor element. The first of the two pump cells in the direction of inflow of the gas mixture causes oxygen to be transported from the measuring gas space into the reference gas channel. The internal pump electrode of this first oxygen-transporting pump cell is covered with a multilayered structure made of a mixed-conducting metal oxide layer and an electrically insulating aluminum oxide layer, which selectively removes the oxygen present in the gas mixture without changing the concentration of nitrogen oxides. These are then decomposed at the internal pump electrode of the second pump cell and the oxygen released in doing so is pumped off. The pump current of the second pump cell is used as a measure of the concentration of nitrogen oxides contained in the gas mixture.

A gas sensor for determining the $NO_x$ concentration in gas mixtures is also known from European Published Patent Application No. 678 740. It includes two measuring gas spaces with one pump cell each, which are arranged adjacent to each other in a layer plane of a planar ceramic substrate. The measuring gas flows through a diffusion opening into the first measuring gas space in which a first pump cell is located. The first pump cell is used in the first measuring gas space to set a predetermined oxygen partial pressure by pumping oxygen in or out. A concentration cell also situated in the first measuring gas space makes it possible to maintain a constantly low oxygen partial pressure in the first measuring gas space by determining the electrical voltage (electromotive force) present at the electrodes of the concentration cell. Via an additional diffusion opening, the gas mixture set to a constant oxygen partial pressure enters the second measuring space. An additional pump cell is situated in the second measuring gas space. Its internal pump electrode is made of rhodium and it makes it possible to decompose nitrogen oxides to $N_2$ and $O_2$. The reduced oxygen arising at the internal pump electrode is pumped off via an applied pump voltage. The pump current of the second pump cell is proportional to the nitrogen oxide concentration of the gas mixture.

In both cases, a constantly low oxygen partial pressure of the gas mixture in the sensor element must be set in an elaborate manner before the nitrogen oxides can be determined with the internal pump electrodes used in them.

SUMMARY OF THE INVENTION

The gas sensor according to the present invention has the advantage that an electrochemical measuring cell, the $NO_x$-sensitive electrode (which is made of a material that makes it possible to determine the nitrogen oxide concentration in a gas mixture reliably even at high oxygen partial pressures), may be used to determine the nitrogen oxide concentration in the measuring gas. This may make it unnecessary to install oxygen-transporting pump cells into the sensor element and therefore may considerably simplify the sensor design.

The use of the $NO_x$-sensitive pump cell according to the invention may make it possible to omit the incorporation of a measuring gas space and a reference gas channel into the sensor element on which the gas sensor is based since the $NO_x$-sensitive pump electrode as well as the counter-electrode may be directly exposed to the exhaust gas. Of particular advantage may be a sandwich arrangement of both electrodes one above the other on the wide surface area of the sensor element.

If a reference gas channel is provided in the sensor element, a reference electrode situated there together with the $NO_x$-sensitive electrode may make it possible to determine the nitrogen dioxide concentration of the gas mixture simultaneously using a voltage measurement as an alternative.

BRIEF DESCRIPTION OF THE DRAWINGS

FIG. 1 shows a cross section through the wide surface area of a sensor element on which the gas sensor according to an exemplary embodiment of the invention is based.

FIGS. 2 and 3 show a sensor element according to alternative exemplary embodiments.

DETAILED DESCRIPTION

FIG. 1 shows a basic structure of an exemplary embodiment of a planar sensor element 10 of an electrochemical gas sensor. Sensor element 10 may have a plurality of oxygen ion-conducting solid electrolyte layers 11a, 11b, 11c, 11d, 11e and 11f. Solid electrolyte layers 11a–11f may be designed as ceramic films and may form a planar ceramic body. The integrated form of the planar ceramic body of sensor element 10 may be produced by laminating together the ceramic films printed with functional layers and subsequently sintering the laminated structure. Each of solid electrolyte layers 11a–11f may be made of oxygen ion-conducting solid electrolyte material such as, for example, $ZrO_2$ partially or fully stabilized with $Y_2O_3$.

Sensor element 10 may contain a measuring gas space 13 and, for example, a reference gas channel 19 in an additional layer plane 11d, in which one end of the reference gas channel may lead out from the planar body of sensor element 10 and may be in contact with an atmosphere of air.

Moreover, a resistance heater 40 may be embedded in the ceramic body of sensor element 10 between two electrical insulation layers. The resistance heater may be used to heat sensor element 10 to the required operating temperature.

In addition, sensor element 10 may have a gas inlet opening 21 which may conduct the measuring gas into first measuring space 13. Gas inlet opening 21 may be, for example, situated in the same layer as measuring gas space 13. A first diffusion barrier 23 of, for example, porous ceramic material may be formed at the inlet to first measuring gas space 13 downstream of gas inlet opening 21 in the direction of diffusion of the measuring gas.

An internal $NO_x$-sensitive electrode 31 may be situated in the measuring gas space 13. Associated external electrode 32 may be located in reference gas channel 19. Both electrodes 31, 32 may be interconnected with a pump cell. Electrode 32 may be made of a catalytically active material, for example, platinum. The electrode material for electrode 32 may be used as a cermet in order to sinter it to the ceramic films. Electrodes 31, 32 are contacted via printed conductors, which are guided between solid electrolyte layers 11a and 11b and are connected to the wide surface area of the sensor element via throughplating.

In order to ensure that the nitrogen oxides contained in the gas mixture are completely decomposed into nitrogen and oxygen on $NO_x$-sensitive electrode 31, $NO_x$-sensitive electrode 31 may be made of a catalytically active, oxide material, for example, from a lanthanum-containing perovskite of the composition $La_{1-x} Sr_x CO_{1-y} Cu_y O_{3-\delta}$. Traditionally, electrodes of this type may be produced from rhodium or a platinum-rhodium alloy. The latter may only allow a reliable determination of the concentration of nitrogen oxides at very low oxygen concentrations of, for example, 0.02 ppm in the gas mixture and therefore may be usable only in sensors that remove the greatest proportion of the oxygen contained in the gas mixture electrochemically (see European Published Patent Application No. 678 740).

The electrode material of an exemplary embodiment of the present invention, which may include a lanthanum-containing perovskite, may permit a determination of the concentration of nitrogen oxides even at a 2 to 20% concentration of oxygen in the gas mixture. Although the nitrogen oxides may be present in these oxygen-rich gas mixtures at an unfavorable ratio compared to oxygen of 1:1000 to 1:10000, a linear dependence of the pump current flowing in the pump cell on the nitrogen oxide concentration may be observed when lanthanum-containing perovskite is used. The oxygen present in the gas mixture may be observed only in the form of a slightly elevated baseline which may be hardly subject to change even when the oxygen concentration varies greatly.

This characteristic may be all the more unexpected since previously a perovskite of the same composition may have only been used as an oxygen-selective protective layer for pump cells for the removal of molecular oxygen from gas mixtures (see German Published Patent Application No. 196 52 968). Only molecular oxygen may be absorbed on this protective layer while it may be impossible to catalytically decompose nitrogen oxides. However, the protective layer may be present as an electrically insulating metallic oxide layer and no pump voltage may be applied to it.

The high measuring accuracy of the lanthanum-containing perovskite used according to an exemplary embodiment of the present invention as an $NO_x$-sensitive electrode 31 even at high oxygen concentrations in the gas mixture may make it possible as an alternative to arrange this electrode on the wide surface area of sensor element 10 directly exposed to the gas mixture and thus eliminate the incorporation of a measuring gas space 13 in the sensor element. If, for example, external electrode 32 is also formed on the wide surface area of the sensor element exposed to the gas mixture, the sensor design may be further simplified since a reference gas channel may be omitted also. A sensor element of this design is shown in FIG. 2. To protect against contamination, electrodes 31, 32 may be additionally provided with a porous gas-permeable protective layer 35 made of $CeO_2$, for example.

An exemplary embodiment of the invention may provide that electrodes 31, 32 are not situated adjacent to each other on the wide surface area of the sensor element, as shown in FIG. 2, but rather on top of each other as in a sandwich and separated by a porous, gas-permeable and oxygen ion-conducting solid electrolyte layer 37. An exemplary embodiment of this type is shown in FIG. 3. The arrangement of a measuring and a reference electrode in superimposed layers on the wide surface area of a sensor element may also be customary in mixed potential sensors.

If the incorporation of a reference gas channel in the sensor element is not omitted, a reference electrode 33 situated in it according to the exemplary embodiment illustrated in FIG. 3 may, for example, be interconnected with $NO_x$-sensitive electrode 31 to form a concentration cell. This may allow the simultaneous determination of the nitrogen oxide concentration by an amperometric method using the pump cell consisting of electrodes 31 and 32 and by a potentiometric method using the potential difference formed between electrodes 31 and 33.

The use of a lanthanum-containing perovskite may not be limited to the explained exemplary embodiments but rather this material may also be used in conventional nitrogen oxide sensors having one or more measuring gas spaces and one or more pump cells and concentration cells.

As a result of the good oxygen tolerance of the sensor element of the exemplary embodiment of the present invention even at atmospheric oxygen concentrations, it may also be conceivable to use the sensor element in air quality sensors in addition to determining nitrogen oxide concentrations in exhaust gases of internal combustion engines.

What is claimed is:

1. A gas sensor system for determining a concentration of nitrogen oxide in a gas mixture, comprising:
    a gas sensor; and
    a device configured to detect nitrogen oxide in conjunction with the gas sensor amperometrically;
    said gas sensor comprising at least one electrochemical measuring cell, a measurement signal of the at least one electrochemical measuring cell determining the concentration of the gas component, the at least one electrochemical measuring cell including a first electrode and at least one additional electrode, wherein at least one of the first electrode and the at least one additional electrode is applied to a solid electrolyte made of $ZrO_2$, which is partially or fully stabilized by $Y_2O_3$, at least one of the first electrode and the at least one additional electrode including a material that at least catalytically decomposes a nitrogen oxide;
    wherein the material includes a lanthanum-containing perovskite having the composition $La_{1-x} Sr_x Co_{1-y} Cu_y O_{3-\delta}$; and
    wherein the first electrode and the at least one additional electrode are interconnected as a pump cell; and
    a measured pump current measured by the device connected to the pump cell includes a measure of a concentration of the nitrogen oxide present in the gas mixture.

2. The gas sensor system according to claim 1, wherein:
    the first electrode is situated in a measuring gas space integrated in the gas sensor, the measuring gas space contacting the gas mixture via a gas inlet; and
    the first electrode includes the material.

3. The gas sensor system according to claim 1, wherein:
    the first electrode is situated on a surface area of the gas sensor exposed to the gas mixture; and
    the first electrode includes the material.

4. The gas sensor system according to claim 3, wherein:
    the at least one additional electrode is situated on the surface area of the gas sensor.

5. The gas sensor system according to claim 1, wherein:
    the first electrode and the at least one additional electrode are situated on a surface area of the gas sensor exposed to the gas mixture;

the first electrode includes the material; and the gas sensor includes a reference gas channel, a reference electrode being situated within the reference gas channel, the reference electrode connected with the first electrode to form a concentration cell.

6. The gas sensor system according to claim 5, wherein:

a further solid electrolyte layer is applied to the at least one additional electrode; and the first electrode is applied to the further solid electrolyte layer.

7. A method of using a gas sensor including at least one electrochemical measuring cell to determine the concentration of $NO_x$ in a gas mixture, a measurement signal of the at least one electrochemical measuring cell determining a concentration, the at least one electrochemical measuring cell including a first electrode and at least one additional electrode applied to a solid electrolyte made of $ZrO_2$, which is partially or fully stabilized by $Y_2O_3$, at least one of the first electrode and the at least one additional electrode including a material that at least catalytically decomposes a nitrogen oxide, the material including a lanthanum-containing perovskite having the composition $La_{1-x} Sr_x Co_{1-y} Cu_y O_{3-\delta}$, wherein the first electrode and the at least one additional electrode are interconnected as a pump cell, and a measured pump current includes a measure of a concentration of the nitrogen oxide present in the gas mixture, the method comprising:

operating the gas sensor as an air quality sensor for determining the concentration of the nitrogen oxide by measuring the pump current.

8. A method of using a gas sensor including at least one electrochemical measuring cell to determine the concentration of $NO_x$, in a gas mixture, a measurement signal of the at least one electrochemical measuring cell determining a concentration, the at least one electrochemical measuring cell including a first electrode and at least one additional electrode applied to a solid electrolyte made of $ZrO_2$, which is partially or fully stabilized by $Y_2O_3$, at least one of the first electrode and the at least one additional electrode including a material that at least catalytically decomposes a nitrogen oxide, the material including a lanthanum-containing perovskite having the composition $La_{1-x} Sr_x Co_{1-y} Cu_y O_{3-\delta}$, wherein the first electrode and the at least one additional electrode are interconnected as a pump cell, and a measured pump current includes a measure of a concentration of the nitrogen oxide present in the gas mixture, the method comprising:

operating the gas sensor to determine a gas component in an exhaust gas of an internal combustion engine by measuring the pump current.

* * * * *

UNITED STATES PATENT AND TRADEMARK OFFICE
CERTIFICATE OF CORRECTION

PATENT NO.       : 7,052,595 B2
APPLICATION NO.  : 10/149940
DATED            : May 30, 2006
INVENTOR(S)      : Schulte et al.

It is certified that error appears in the above-identified patent and that said Letters Patent is hereby corrected as shown below:

Column 3, line 12, change "$CO_{1-y}$" to --$Co_{1-y}$--

Column 4, line 45, change "$O_{3-\delta}$ ; $_{and}$" to --$O_{3-\delta}$ ; and--

Signed and Sealed this

Nineteenth Day of February, 2008

JON W. DUDAS
*Director of the United States Patent and Trademark Office*